United States Patent [19]
Diery et al.
[11] 3,957,863
[45] May 18, 1976

[54] ANTI-MICROBIALLY ACTIVE SURFACE-ACTIVE AGENTS

[75] Inventors: Helmut Diery, Paris, France; Elmar Schrinner, Wiesbaden, Germany; Kurd Günther, Diedenbergen, Taunus, Germany; Gerhart Schneider, Schneidhain, Taunus, Germany

[73] Assignee: Hoechst Aktiengesellschaft, Frankfurt am Main, Germany

[22] Filed: Nov. 12, 1974

[21] Appl. No.: 523,021

[30] Foreign Application Priority Data

Nov. 16, 1973 Germany .......................... 2357278

[52] U.S. Cl. .......................... 260/534 R; 252/106; 260/534 E

[51] Int. Cl.² .............. C07C 101/24; C07C 101/26

[58] Field of Search .................. 260/534 R, 534 E

[56] References Cited

UNITED STATES PATENTS

| | | | |
|---|---|---|---|
| 3,303,213 | 2/1967 | Kalopissis et al. | 260/534 R |
| 3,773,479 | 11/1973 | Dorn et al. | 260/534 R |
| 3,795,704 | 3/1974 | Diery et al. | 260/534 R |

*Primary Examiner*—Richard L. Raymond
*Attorney, Agent, or Firm*—Connolly and Hutz

[57] ABSTRACT

New compounds of the general formula II

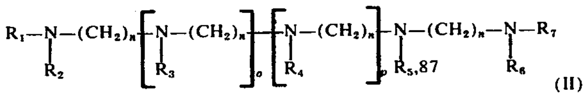

(II)

in which one or two of the radicals $R_i$ (i = 1 to 7) stands for a linear or branched alkyl or alkenyl radical of 8 to 18 carbon atoms, one or two of the radicals $R_m$ (m = 2 to 6, m being ≠ i) stands for the radical of the formula A

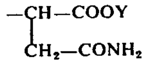

(A)

and the other radicals $R_k$ (k = 1 to 7, k being ≠ i, m) stand for hydrogen or methyl, Y stands for hydrogen or an alkali metal ion, n is 2 or 3 and o and p are 0 or 1, their use as anti-microbially active surfactants in washing and cleansing compositions and disinfectants, and a process for preparing those compounds of formula II.

6 Claims, No Drawings

ANTI-MICROBIALLY ACTIVE SURFACE-ACTIVE AGENTS

The present invention relates to anti-microbially active compounds having surface-active properties. These compounds retain their anti-microbial action, i.e. their activity towards bacteria, fungi, actinomycetes and viruses, in the presence of surface-active cleansing compositions, especially textile cleansing compositions.

The known surface-active compounds which have good cleansing properties, in general, have no anti-microbial action. On the other hand, certain cationic compounds, for example quaternary ammonium compounds, which are active against certain bacteria types have only moderate cleansing properties. Hitherto, if the combating of bacteria and fungi was to be achieved simultaneously with cleansing, two separate treatments have generally been necessary, namely a normal washing step and a subsequent, separate treatment of the washed material with an anti-microbial agent in a suitable physical form, for example a solution or dispersion.

In many cases it would be more practical and effective if the cleansing composition and the anti-microbial agent could be used simultaneously or, if desired, if both effects could be combined in a single preparation. Attempts have already been made in this field; however, they have not provided satisfactory results. One reason for the past failures can be seen in the reciprocal action which occurs between most anti-microbial agents and the synthetic surfactant. This incompatibility results either in a diminished cleansing effeciency of the surface-active agent or in the partial or complete inactivity of the anti-microbial agent or in both.

Striking examples of such a reciprocal action occur in preparations which contain anionic surface-active cleansing compounds, inclusively soaps and non-soap compounds, as well as the hitherto known anti-microbial agents. In these cases, the cleansing effeciency of the anionic cleansing composition is usually worse than when used alone and also the activity of the anti-microbial agents is substantially inferior than when used alone. A similar reciprocal action is also encountered in preparations which contain non-ionic, cationic or amphoteric surface-active agents.

In recent times some anti-microbial agents which are compatible with certain cleansing compositions have been available (for example bromosalicyl anilide and carbanilide), which confers to soaps and synthetic cleansing compositions an inhibiting or destroying action towards grampositive bacteria, for example, staphylococcus aureus, bact. ammoniagenes and lactobacillus casei. On the other hand, suitable agents which would be compatible with soap and cleansing compositions and give them a considerable action also against the resistent gramnegative bacteria, for example escherichia coli, proteus mirabilis and pseudomonas aeruginosa, and fungi, for example candida albicans, are still not available.

Until now no prediction has been possible as to how a given anti-microbial agent will behave in a washing preparation. Some of the numerous unknown factors which influence the behaviour of the agent are, for example, the complex nature of the cleansing composition itself, the dirt present, the variety of the textiles to be cleaned, and the different ionogenic properties of the compounds.

Suitable anti-microbial agents are especially wanted for use in preparations of cleansing compositions intended for laundering purposes. For this purpose it is desirable that a residue of the disinfection agent remains on the textile after the laundering, so that a long-lasting action results. Therefore, for the laundering of textiles, anti-bacterial agents are desired which are applicable in washing solutions and remain behind on the textile, and thus prevent the reproduction of bacteria and/or fungi as well as the penetration of body odor into the textile. A similar treatment is especially advantageous with underwear, especially when the adhering anti-microbial agent is also active against gram-negative bacteria. Anti-bacterial agents, which are compatible with synthetic cleansing compositions, are also used in deodorizing and cosmetic soaps and sprays. The latter application requires that the active compound has an adhesiveness to human skin, so that a residue of the agent remains behind on the skin after the washing-treatment and might thus inhibit the microbial population, which decompose sweat with the simultaneous formation of odor.

In recent times there have been proposed as antimicrobially active surface-active agents diamines of the general formula I

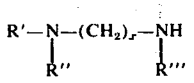
(I)

in which R′ is an alkyl or alkenyl radical of 8 to 18 carbon atoms, R″ and R‴ each is hydrogen or the radical of the formula A

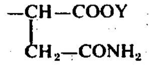
(A).

in which case at least one of the radicals R″ or R‴ is that radical of the formula A and Y is hydrogen or an alkali metal and x is 2 or 3.

It has now been found that ampholytic compounds of the general formula II

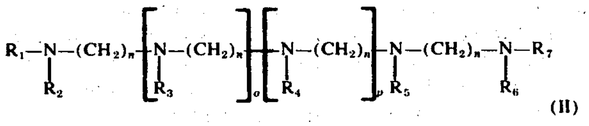
(II)

are also excellent antimicrobially active surface-active substances that retain their antimicrobial activity even in the presence of other surface-active washing and cleansing agents. The new ampholytic compounds of the invention have an improved stability towards hard water as well as, in general, an improved solubility in water as compared with the diamines of the formula I; for this reason they are more suitable for being worked to commercial preparations and concentrates. A further advantage is their greater activity against numerous fungi and bacteria at a relatively low concentration.

In the general formula II one or two, preferably one of the radicals $R_i$ ($i = 1 - 7$), especially $R_1$, stand for a linear or branched alkyl or alkenyl radical of 8 – 18 carbon atoms, one or two, preferably one of the radicals $R_m$ ($m = 2 - 6$, with $m \neq i$), especially $R_6$, stand for the radical of the formula A

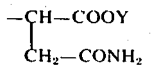

(A)

and the other radicals $R_k$ ($k = 1 - 7$, with $k \neq i, m$) stand for hydrogen or methyl, preferably hydrogen, Y stands for hydrogen or an alkali metal ion, n is 2 or 3 and o and p are 0 or 1, preferably 0.

One or two of the radicals $R_i$ of the new ampholytic compounds denotes a lipophilic group which may be in the form of an unsaturated or saturated linear or branched aliphatic hydrocarbon radical of 8 to 18 carbon atoms, especially 10 to 16 carbon atoms, preferably in the radical $R_1$, in the end position of the general formula II.

Especially preferred are compounds of the formula II mentioned above wherein one of the radicals $R_i$ is a linear alkyl radical having expecially 10 to 14 carbon atoms.

The ampholytic compounds of the invention may be prepared by reacting about 1 mol of a preferably not methylated N-alkyl-polyalkylene-polyamine of the general formula III

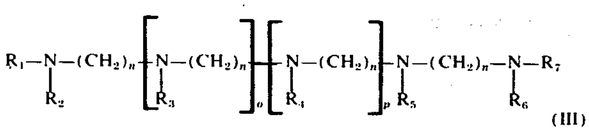

(III)

in which one or two of the radicals $R_1$, $R_2$, $R_3$, $R_4$, $R_5$, $R_6$ and $R_7$ each stands for a linear or branched alkyl or alkenyl radical of 8 to 18 carbon atoms and the other radicals $R_1$ to $R_7$ each stands for hydrogen or methyl, in which case at least one of the radicals $R_1$ to $R_7$ stands for hydrogen and n, o and p are defined as in formula II with 1 to 2 mols of maleic acid semi-amide, in an aqueous or aqueous alcoholic phase, advantageously at an elevated temperature above 20°C, especially at 60° – 100°C, to accelerate reaction. Instead of the maleic acid semi-amide the salts thereof may also be used for reaction, especially the alkali metal or ammonium salts, preferably the ammonium salt thereof, since this is easily obtainable and, upon reaction, sets free ammonia so that the ampholytic compound is obtained directly in the form of the inner salt. When alkali metal salts, for example the sodium or potassium salt, of the maleic acid semi-amide are reacted with the polyamine, the reaction products are obtained in the form of the corresponding alkali metal salt that can be converted, where required, into the inner salts by adding an acid until the pH-value of the equipotential point has been reached.

The reaction with maleic acid semi-amide or the salts thereof is preferably carried out with N-alkylpolyalkylene-polyamines of the formula IV $$R'-[NH(CH_2)_n]_qNH_2 \qquad (IV)$$

in which R' stands for an alkyl or alkenyl radical of 8 to 18 carbon atoms, n is 2 or 3 and q is 2 – 4, preferably 2. Preferably, less than 2 mols, especially about 1 mol of maleic acid semi-amide or the salts thereof are used per mol of polyamine in this reaction.

In the above preparation of the new ampholytic compounds of the invention generally mixtures of isomer compounds are obtained that correspond to the general formula II, the preponderant part thereof, i.e. more than 60 percent by weight, in general, more than 70 percent by weight, consisting of compounds which contain the radical of the formula A and an alkyl or alkenyl radical of 8 to 18 carbon atoms upon the nitrogen atoms in end position, in the positions of the radicals $R_6$ and $R_1$.

Those isomer mixtures contain minor amounts of compounds in which the radical of the formula A or-/and an alkyl or a alkenyl radical of 8 to 18 carbon atoms is placed at a nitrogen atom in inner position. These isomer mixtures can be used as anti-microbially active surfactants as successfully as the new compounds of the formula II.

A special advantage of the ampholytic compounds of the present invention is that they retain their anti-microbial action even in the presence of anionic, cationic, and nonionic surfactants and also in the presence of organic and inorganic builders. The ampholytic compounds of the invention can, therefore, be added to conventional washing agents and cleansing compositions as well as to soft-rinsing agents or can be used in conjunction with such agents.

Surface-active substances and builders, such as are used for the manufacture of washing agents and cleansing compositions together with the novel ampholytic compounds of the invention, are mentioned, for example, in Schwartz, Perry, Berch, "surface-active agents and detergents," Volume II (1958), page 25 to 138 and 288 to 317. The washing agents and cleansing compositions may further contain optical brightening agents, perborates and enzymes without impairing the anti-microbial action of the ampholytic compounds of the invention. In addition, other known additives and diluents, for example perfumes, fluorescence agents, foam-promoting or foam-depressing agents as well as auxiliaries preventing deposits, do not lessen the advantageous action of the ampholytic compounds of the invention.

The ampholytic compounds of the present invention are highly active and hence a small amount is sufficient to give the washing agent or cleansing composition an anti-microbial action. The amount of the ampholytic compounds added to the washing agent or cleansing composition may vary within wide limits. The amount used depends, primarily, upon the antimicrobial effect desired for the washing agent or cleansing composition. An amount of from 0.1 to 10 percent, calculated on the weight of the washing agent, cleansing composition or soft-rinsing agent is generally employed. The preferred range of concentration of the ampholytic compounds is, however, 0.5 to 5 percent by weight, calculated on the washing agent or cleansing composition. The upper limit of the amount of the ampholytic compounds of the invention is mainly dependent on economic considerations and, if necessary, upon the solubility properties. An increase in concentration augments, as is to be expected, the anti-microbial action of the washing agent or cleansing composition.

The ampholytic compounds of the present invention can be incorporated into washing or cleansing preparations according to any method provided an even distribution in the entire mass is guaranteed. In doing so the good compatibility of the ampholytic compounds with the above-mentioned washing agents or cleansing compositions in the form of, for example, bars, liquids, flakes and granules becomes apparent. Even under the influence of sun-light the ampholytic compounds of the invention do not cause any decolouration of the washing agents or cleansing compositions. In this respect, the ampholytic compounds of the invention are superior to the known anti-microbial additives based on bisphenolic compounds.

A further advantage associated with the use of the ampholytic compounds of the present invention is that they are substantively absorbed by fabrics comprising, for example, wool or cotton during washing or rinsing with a washing or rinsing agent containing a compound of the invention. Thereby, the textiles obtain a long-lasting anti-microbial protection.

The anti-microbial action on textiles is tested by the textiles protection test. This test essentially comprises first washing a sample with a known washing liquor and subsequently treating it in an aqueous solution with a soft-rinsing agent which contains the anti-microbially active agent, drying the sample and placing it on a nutrient agar, to which the bacteria used for the test have been added. After a short time the samples are removed and the agar plates incubated at 37°C for 24 hours. Due to the anti-bacterial action, no growth of bacteria is observed on the bearing surfaces and their surroundings.

The ampholytic compounds of the present invention cover such a broad range of action that they may be used, for example, as disinfection agents, and more especially, for medicinal and hygienic purposes. Their use in cleansing compositions, for example heavy duty or fine washing agents and soft-rinsing agents, is of special interest since their anti-bacterial action is retained in the presence of such agents. This favourable behaviour of the ampholytic compounds of the invention renders possible the combination of a washing agent, cleansing composition or rinsing agent and an anti-microbially active agent in one preparation.

The following Examples serve to illustrate the invention, the parts and percentages being by weight unless stated otherwise.

EXAMPLE 1 A.

A solution of 19.8 parts of the ammonium salt of maleic acid semi-amide (prepared from maleic acid anhydride and gaseous ammonia in chloroform) in 92 parts of water is stirred at 80° – 85°C for 3 hours with 44.1 parts of N-lauryldiethylene triamine (having a content of basic nitrogen of 14.3 percent). During the reaction ammonia develops. The liquid is concentrated under reduced pressure (in a rotary evaporator) by distilling off water. The pasty residue is dried in vacuo at a temperature of about 50°C. The compound obtained essentially (more than 75 percent) consists of the formula

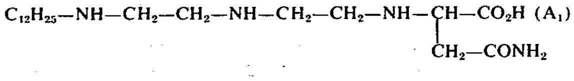
$(A_1)$ and of portions of about 20 percent of a compound of the formula

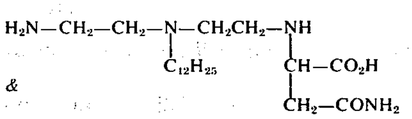
$(A_2)$ and very slight portions of a compound of the formula

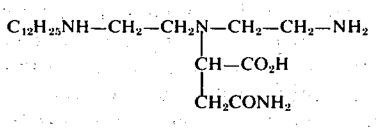
$(A_3)$ and is in the form of a yellowish wax-like substance which can be ground to a fine powder. Its basic nitrogen content is 10.5 percent (calculated: 10.7 percent).

B.

73.6 Parts of N-dodecyl-tetraethylene pentamine (having a basic nitrogen content of 15.6 percent) and 26.4 parts of the ammonium salt of maleic acid semi-amide in 141 parts of water are stirred at 85°C for 3 hours. The alkaline yellow clear reaction solution may be adjusted to pH 6.5 – 7.5 with acetic acid and can be used as such. A plastic mass can be obtained from the solution by drying. The yellow product (B) so obtained is a mixture of analogous isomer compounds consisting essentially of the compound of the formula

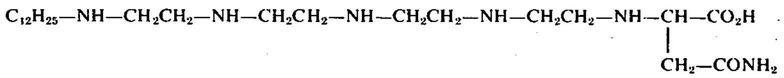

The substance has a basic nitrogen content of 14.3 percent (calculated: 14.45 percent). C.

A mixture of 26.4 parts of the ammonium salt of maleic acid semi-amide, 68.0 parts of N-dodecyl-triethylene tetramine (having a basic nitrogen content of 16.2 percent) and 133 parts of water are stirred at 85° – 90°C for 3 hours. The alkaline reaction solution can be adjusted at pH 6.5 – 7.5 with acetic acid and can be used as such. A plastic mass can be obtained from the solution by drying. The fairly yellow product (C) so obtained is a mixture consisting essentially of the compound of the formula

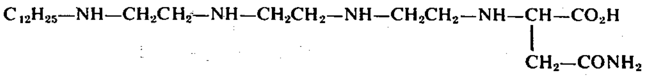

and has a basic nitrogen content of 12.1 percent (calculated: 12.3 percent). D.

A mixture of 26.4 parts of the ammonium salt of maleic acid semi-amide, 66.5 parts of N-lauryl-N'-methylimino-bis-propyl amine having a basic nitrogen content of 12.6 percent and 134 parts of water are stirred at 80° –85°C for 3 hours. The alkaline yellow clear solution can be adjusted at pH 6.5 – 7.5 with acetic acid and can be used as such. A pulverulent fairly yellow product (D) can be obtained from the solution by drying. This product corresponds to the formula

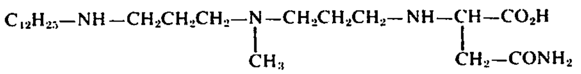

Its basic nitrogen content is 9.3 percent (calculated: 9.4 percent).

The ampholytic compounds of the invention possess a surprisingly varied anti-microbial activity. They are bacteriostatically and bactericidally active against gram-positive and gram-negative organisms. Moreover, they have a fungistatic activity. The good bacteriostatic and fungistatic activity of the ampholytic compounds of the invention is demonstrated by the data summarized in Table II. The results of these tests show the surprisingly broad anti-microbial activity range of the ampholytic compounds as compared with the typical known surface-active ampholytic compounds (cf. for example, Kurt Lindner - Tenside-Textilhilfsmittel-Waschrohstoffe - volume I (1964), pages 1031 – 1032).

Comparison product Z:

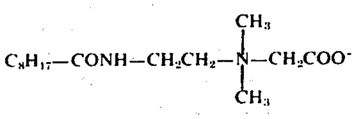

The results were obtained in a series dilution test, which was performed in agreement with the procedure of "Richtlinien fur die Prufung chemischer Desinfektionsmittel" (Gustav Fischer Verlag, Stuttgart, Germany, (1969)), edited by the German Society for Hygiene and Microbiology. In these tests, the minimal inhibition concentration (MIC) has been determined. This is the minimal concentration ascertained in the pure dilution test, in the weight unit per cubic centimeter of the test solution of an antimicrobially active substance, at which no increase of the examined organisms could be observed.

Table I

Minimum inhibition concentration

| | product A | product B | product C | product D | product Y | comparison product Z |
|---|---|---|---|---|---|---|
| Staph.aureus IG 511 | 25.0 γ/ml | 25.0 γ/ml | 25.5 γ/ml | 12.5 γ/ml | 32 γ/ml | 160 γ/ml |
| Strept.pyogenes 308 A | 6.25 γ/ml | 6.25 γ/ml | 6.25 γ/ml | 6.25 γ/ml | — | — |
| Strept. aecium D | 15.6 γ/ml | 15.6 γ/ml | 7.8 γ/ml | 6.25 γ/ml | 40 γ/ml | — |
| E. coli 055 | 62.5 γ/ml | 125.0 γ/ml | 62.5 γ/ml | 31.5 γ/ml | 80 γ/ml | ineffective |
| Proteus mirabilis | 1.25 mg/ml | 1.0 mg/ml | 1.0 mg/ml | 1.0 mg/ml | 5 mg/ml | ineffective |
| Pseudomonas aeruginosa | 62.5 γ/ml | 39.1 γ/ml | 39.1 γ/ml | 39.1 γ/ml | 80 γ/ml | ineffective |

EXPLANATIONS:

Product A: 1-dodecyl-N-(2-carbamoyl-1-carboxyethyl)-1,4,7-triazaheptane,

Product B: 1-dodecyl-N-(2-carbamoyl-1-carboxyethyl)-1,4,7,10,13-pentaazatridecane, Product C: 1-dodecyl-N-(2-carbamoyl-1-carboxyethyl)-1,4,7,10-tetraazadecane, Product D: 1-dodecyl-5-methyl-9-(2-carbamoyl-1-carboxyethyl)-1,5,9-triazanonane, Comparison product Y:

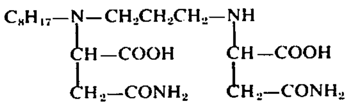

The bactericidal activity (bactericidal concentration) was also tested in germ suspension tests according to the criteria indicated above. The results of these tests are represented in Table II.

EXAMPLE 2

Further examples of the ampholytic compounds of the invention are summarized in the following Table. (These compounds are prepared according to the indications made with reference to products A to D).

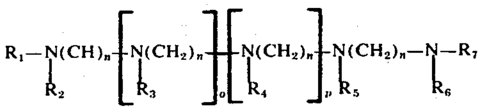

X = 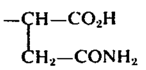

| | n | o | p | $R_1$ | $R_2$ | $R_3$ | $R_4$ | $R_5$ | $R_6$ | $R_7$ | basic nitrogen found | basic nitrogen calculated |
|---|---|---|---|---|---|---|---|---|---|---|---|---|
| E | 3 | 1 | 1 | $C_{18}H_{37}$ | H | H | $CH_3$ | H | H | X | 10.8% | 11.0% |
| F | 3 | 1 | 0 | $C_{18}H_{37}$ | H | $CH_3$ | — | H | H | X | 9.2% | 9.5% |
| G | 3 | 1 | 1 | $C_{18}H_{37}$ | H | H | H | H | H | X | 11.0% | 11.1% |
| H | 2 | 1 | 0 | $C_{18}H_{37}$ | H | H | — | H | H | X | 10.2% | 10.4% |
| F | 2 | 1 | 0 | $C_8H_{17}/C_{10}H_{21}$[1] | H | H | — | H | H | X | 15.9% | 16.2% |
| K | 2 | 0 | 0 | $C_{12}H_{25}$ and | {X | — | — | H | H | X} | 8.4% | 8.25% |
| | | | | | {H | — | — | X | H | X} | | |
| L | 3 | 0 | 0 | $C_{12}H_{25}$ | H | — | — | H | H | X | 9.0% | 9.2% |
| M | 2 | 0 | 0 | coconut oil alkyl | H | — | — | H | H | X | 9.8% | 9.6% |
| N | 2 | 0 | 0 | $C_8H_{17}$ | H | — | — | H | H | X | 11.4% | 11.5% |
| 0 | 3 | 0 | 0 | $C_8H_{17}$ | $C_8H_{17}$ | — | — | H | H | X | 8.5% | 8.7% |
| P | 2 | 0 | 0 | $C_8H_{17}$ and | {H | — | — | X | H | $C_8H_{17}$} | 9.0% | 9.2% |
| | | | | | {H | — | — | H | X | $C_8H_{17}$} | | |

[1] 44% $C_8H_{17}$ + 56% $C_{10}H_{21}$

[2] distribution of alkyl chain: 7% $C_8$, 6% $C_{10}$, 51% $C_{12}$, 19% $C_{14}$, 8% $C_{16}$ and 9% $C_{18}$

EXAMPLE 3

A synthetic heavy-duty detergent, which has a granular builder, consists of the following components:

8.00 percent of the sodium salt of secondary alkanesulfonic acid (average molecular weight 328), prepared by sulfoxidation of a mixture of n-paraffins with 13 to 18 carbon atoms,
5.00 percent of an addition product of 15 mols of ethyleneoxide to 1 mol of tallow-fatty alcohol
3.00 percent of sodium soap
37.00 percent of sodiumtripolyphosphate
7.00 percent of sodium metasilicate
3.00 percent of magnesium silicate
4.00 percent of carboxylmethyl cellulose
0.30 percent of an optical brightener
0.15 percent of perfume oil
20.00 percent of sodium-perborate,
the remainder, to 100 percent of water.

1.0 percent or 0.01 percent of product A were added to said detergent mixture for obtention of the antimicrobial effect desired.

In solutions of 0.9 g per liter of the pure detergent mixture (without the disinfection component), the minimum inhibition concentration of the ampholytic compounds of the invention was determined according to the above-specified method and compared with the MIC-values found for the detergent alone. It appeared that the heavy-duty detergent practically did not impair the antimicrobial activity of the ampholytic compound A. The results of the tests are compiled in Table III.

Table III

Minimum inhibition concentration [γ/ml] in the presence of heavy-duty detergents

| Type of germ | Product A alone | Detergent alone | Product A in detergent solution of 0.9 g/l |
|---|---|---|---|
| Str. faecalis | 15.6 | 1250 | 31.5 |
| E. coli | 62.5 | 1250 | 125.0 |

The same tests were performed on heavy-duty detergents of the above-mentioned composition which, however, contains instead of 8.0 percent of the secondary sodium salt of alkanesulfonic acid:

a. 8.00 percent of a mixture of equal parts of the sodium salts of an α-olefin sulfonate having 15 to 18 carbon atoms and of the secondary alkane-sulfonate and
b. 8.00 percent of the sodium salt of dodecyl-benzene-sulfonic acid.

In both cases, no impairment of the anti-microbial activity of the ampholytic compounds of the invention by the detergents was ascertained.

EXAMPLE 4

A high-duty detergent consists of the following components:

10.00 percent of an addition product of 8 mols of ethylene oxide on 1 mol of coco fatty acid,
10.00 percent of an addition product of 5 mols of ethylene oxide on 1 mol of isotridecyl alcohol,
40.00 percent of sodium tripolyphosphate,
5.00 percent of sodium silicate,
10.00 percent of calcined sodium carbonate,
2.00 percent of carboxymethyl cellulose and
the remainder to 100 percent of sodium sulfate. To render the detergent antimicrobially active, an ampholytic compound of the invention, for example product A, may be added in an amount depending on the effect desired.

In solutions of 5 g per liter of the pure high-duty detergent, the minimum inhibition concentration for product A was determined in a manner analogous to Example 2 and compared with the values ascertained for the detergent alone and for product A alone. The results obtained are compiled in Table IV.

Table IV

Minimum inhibition concentration [γ/ml] in the presence of high-duty detergents

| Type of germ | Product A alone | high-duty detergent alone | Product A in high-duty detergent solution of 1 g/l |
|---|---|---|---|
| Str. faecalis | 15.6 γ/ml | 5 mg/ml | 6.25 γ/ml |
| E. coli 055 | 62.5 γ/ml | ineffective | 62.5 γ/ml |

The results show that the addition of an ampholytic compound of the invention imparts an excellent antimicrobial activity to the high-duty detergent, the action of the ampholytic compound being even increased, in some cases, by the components of the high-duty detergent.

EXAMPLE 5

A soft-rinsing agent has the following composition:

6.0 percent of distearyl-dimethyl-ammonium chloride,
0.5 percent of an addition product of 12 mols of ethylene oxide on 1 mol of oleyl alcohol,
0.5 percent of optical brighteners,
0.05 percent of perfume oil and
the remainder to 100 percent water.

By addition of an ampholytic compound of the invention, e.g. product A, this said soft-rinsing agent obtained an excellent anti-microbial action.

In the same manner as in Example 3, in solutions of 0.3 g per liter of the pure soft-rinsing agent the minimum inhibition concentration of the ampholytic compound of the invention was determined and compared with the values ascertained for the soft-rinsing agent alone and the ampholytic agent singly.

The results are represented in Table V. They show that the anti-microbial action is not impaired by the components of the soft-rinsing agent.

Table V

| Minimum inhibition concentration in the presence of soft-rinsing agents | | | |
|---|---|---|---|
| Type of germ | Product A alone | Soft-rinsing agent alone | Product A in soft-rinsing agent solution of 0.3 g/l |
| Str. faecalis | 15.6 γ/ml | 1.25 mg/ml | 25.0 γ/ml |

EXAMPLE 6

A liquid foot-washing agent of following composition is prepared:

30 percent of an addition product of 10 mols of ethylene oxide on 1 mol of coco fatty alcohol,
0.2 percent of perfume and dyestuffs,
1 percent of product A and
remainder to 100 percent water.

Due to the fungicidal activity of the ampholytic compound, the foot-washing agent shows excellent action against foot fungi. The anti-microbial action of the ampholytic compound is not impared by the remaining components of the foot-washing agent.

EXAMPLE 7

A high-duty detergent containing the compounds of the invention as the washing-active and anti-microbially active substance, has the following composition:

12 percent of product A,
8 percent of an addition product of 8 mols of ethylene oxide on 1 mol of coco fatty alcohol,
40 percent of sodium tripolyphosphate,
5 percent of sodium silicate,
10 percent of calcined sodium carbonate,
2 percent of carboxymethyl cellulose and
23 percent of sodium sulfate.

A detergent of this composition showed very good washing effects on wool, polyamide, polyester and other fibers and reduced the germ content of the washing liquor.

Table II

| | Bactericidal concentration | | | | | |
|---|---|---|---|---|---|---|
| | Product A | | Product B | | Product C | |
| | after 5 min. | after 15 min. | after 10 min. | after 15 min. | after 5 min. | after 15 min. |
| Staph.aureus SG 511 | 125 γ/ml | 125 γ/ml | 500 γ/ml | 500 γ/ml | 2.0 mg/ml | 250 γ/ml |
| E.coli 055 | 250 γ/ml | 125 γ/ml | 250 γ/ml | 250 γ/ml | 250 γ/ml | 250 γ/ml |
| Proteus mirabilis | 500 γ/ml | 250 γ/ml | 1.0 mg/ml | 1.0 mg/ml | 500 γ/ml | 500 γ/ml |
| Ps. aeruginosa | 125 γ/ml | 125 γ/ml | 250 γ/ml | 250 γ/ml | 250 γ/ml | 125 γ/ml |

| | Product D | | Comparison product Y | | Comparison product Z | |
|---|---|---|---|---|---|---|
| | after 5 min. | after 15 min. | after 5 min. | after 15 min. | after 5 min. | after 15 min. |
| Staph.aureus SG 511 | 500 γ/ml | 125 γ/ml | 350 γ/ml | 350 γ/ml | ineffective | |
| E.coli 055 | 500 γ/ml | 62.5 γ/ml | 350 γ/ml | 160 γ/ml | ineffective | |
| Proteus mirabilis | 1.0 mg/ml | 500 γ/ml | mg/ml | 5 mg/ml | ineffective | |
| Ps. aeruginosa | 500 γ/ml | 250 γ/ml | 1.25 mg/ml | 350 γ/ml | ineffective | |

What is claimed is:

1. A compound of the general formula

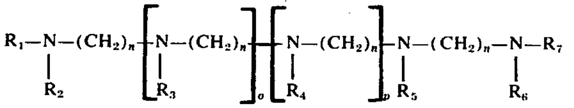

in which one or two of the radicals $R_i$ (i = 1 to 7) stands for a linear or branched alkyl or alkenyl radical of 8 to 18 carbon atoms, one or two of the radicals $R_m$ (m = 2 to 6, m being ≠ i) stands for the radical of the formula

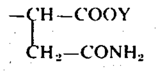

and the other radicals $R_k$ (k = 1 to 7, k being ≠ i, m) stand for hydrogen or methyl, Y stands for hydrogen or an alkali metal ion, n is 2 or 3 and o and p are 0 or 1.

2. A compound as claimed in claim 1, in which $R_1$ stands for a linear or branched alkyl or alkenyl radical of 8 to 18 carbon atoms, $R_6$ stands for the radical of the formula

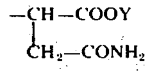

and the other radicals $R_2$ to $R_5$ and $R_7$ each stands for hydrogen or methyl, preferably hydrogen, Y stands for hydrogen or an alkali metal ion, n is 2 or 3, and o and p are 0 or 1.

3. A compound as claimed in claim 1, which is

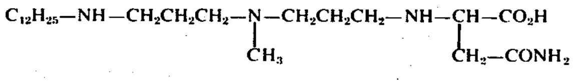

4. A compound as claimed in claim 1, which is

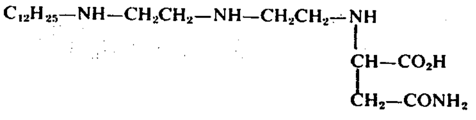

5. A mixture of the formulae $A_1$, $A_2$ and $A_3$,

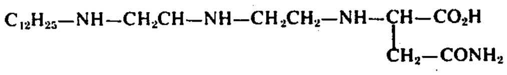
($A_1$)
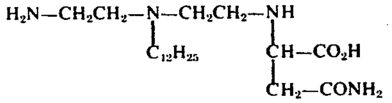
($A_2$)
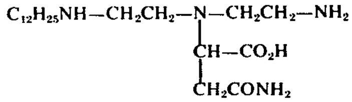
($A_3$)
the mixture containing more than 75 percent by weight of $A_1$ and about 25 percent by weight of $A_2$.
6. A compound as claimed in claim 1 which is
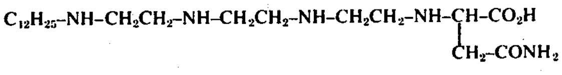
* * * * *